United States Patent
Vartuli et al.

(10) Patent No.: US 7,468,465 B2
(45) Date of Patent: *Dec. 23, 2008

(54) METHOD OF MAKING MIXED METAL OXIDE CONTAINING SULFUR

(75) Inventors: James Clarke Vartuli, Schwenksville, PA (US); Doron Levin, Annandale, NJ (US); Stephen John McCarthy, Center Valley, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 386 days.

This patent is subject to a terminal disclaimer.

(21) Appl. No.: 11/141,482

(22) Filed: May 31, 2005

(65) Prior Publication Data

US 2006/0270883 A1 Nov. 30, 2006

(51) Int. Cl.
*C07C 29/12* (2006.01)
*C07C 27/00* (2006.01)
*C07C 27/18* (2006.01)
*C07C 29/10* (2006.01)
*C07C 29/00* (2006.01)
*B01J 27/02* (2006.01)
*B01J 23/00* (2006.01)

(52) U.S. Cl. ............... 568/889; 568/907; 502/216; 502/302; 502/303; 502/304; 502/349

(58) Field of Classification Search ............ 502/304, 502/217, 216, 302–303, 349; 501/103, 126; 423/213.2, 239.1, 245.1, 247, 518; 585/640; 568/889, 907, 908

See application file for complete search history.

(56) References Cited

U.S. PATENT DOCUMENTS

| | | | |
|---|---|---|---|
| 4,254,290 A | 3/1981 | Chambers et al. | 568/866 |
| 4,320,232 A | 3/1982 | Volkamer et al. | 568/697 |
| 4,395,580 A * | 7/1983 | Juguin et al. | 585/639 |
| 4,398,051 A | 8/1983 | Araki et al. | 585/640 |
| 4,521,638 A | 6/1985 | Kida et al. | 585/640 |
| 4,691,073 A | 9/1987 | Michaelson | 585/639 |
| 5,117,920 A | 6/1992 | Soble | 173/28 |
| 5,171,920 A | 12/1992 | Chaumette et al. | 585/640 |
| 5,177,301 A | 1/1993 | Knifton | 585/855 |
| 5,254,785 A | 10/1993 | Rosenfeld et al. | 585/640 |
| 5,478,543 A | 12/1995 | Murota et al. | 423/263 |
| 5,518,699 A | 5/1996 | Kashnitz et al. | 422/211 |
| 5,532,198 A | 7/1996 | Chopin et al. | 502/304 |
| 5,580,536 A | 12/1996 | Yao et al. | 423/236 |
| 5,580,537 A | 12/1996 | Sextl et al. | 423/335 |
| 5,582,785 A | 12/1996 | Yao et al. | 264/60 |
| 5,607,892 A | 3/1997 | Chopin et al. | 502/304 |
| 5,712,218 A | 1/1998 | Chopin et al. | 502/304 |
| 5,747,401 A | 5/1998 | Cuif | 501/103 |
| 5,908,800 A | 6/1999 | Bonneau et al. | 501/103 |
| 6,124,232 A | 9/2000 | Chang | 502/308 |
| 6,133,194 A | 10/2000 | Cuif et al. | 502/506 |
| 6,150,288 A * | 11/2000 | Suzuki et al. | 501/105 |
| 6,150,299 A | 11/2000 | Umemoto et al. | 502/304 |
| 6,162,757 A | 12/2000 | Chang et al. | 502/302 |
| 6,255,242 B1 | 7/2001 | Umemoto et al. | 501/103 |
| 6,291,719 B1 | 9/2001 | Gao et al. | 568/596 |
| 6,297,406 B1 | 10/2001 | Levin et al. | 568/798 |
| 6,319,876 B1 | 11/2001 | Maier | 502/178 |
| 6,506,705 B2 | 1/2003 | Blanchard et al. | 502/300 |
| 6,552,236 B2 * | 4/2003 | Sakuth et al. | 568/907 |
| 6,605,565 B1 | 8/2003 | Zhang et al. | 502/304 |
| 7,102,037 B2 * | 9/2006 | Levin et al. | 568/908 |
| 2003/0050189 A1 * | 3/2003 | Morikawa et al. | 502/304 |

FOREIGN PATENT DOCUMENTS

| | | |
|---|---|---|
| JP | 59010528 | 1/1984 |
| JP | 6072904 | 3/1994 |
| WO | WO 03/037506 | 5/2003 |
| WO | WO 2005/066101 | 7/2005 |

OTHER PUBLICATIONS

Yan, Xiu-Ru et al., "Photocatalytic Degradation of Dimethyl Dichlorovinyl Phosphate Over Nanosixed SO42-/Ce-TiO2", Kexu Chubanshe, vol. 20, No.7, pp. 668-671, (2003) Abstract Only.

Zi, Jun-Feng, "Synthesis of n-butyl Acetate Catalyzed by SO42-/TiO2/Ce(IV) solid Superacid" Hecheng Huaxue Bianjibu, vol. 11, No. 3 pp. 277-279, (2003) Abstract Only.

* cited by examiner

*Primary Examiner*—Steven Bos
*Assistant Examiner*—Anthony J Zimmer
(74) *Attorney, Agent, or Firm*—Andrew B. Griffis

(57) ABSTRACT

The invention relates to a method of making Group 3 and Group 4 mixed metal oxide catalyst suitable for the decomposition of ethers to alkenes and alkanols. In an embodiment, it relates to a method of making a cerium-zirconium mixed metal oxide catalyst. In an embodiment, the catalyst made by the process of the invention is used for the production of isopropanol (IPA) from isopropyl ether (IPE).

12 Claims, No Drawings

US 7,468,465 B2

METHOD OF MAKING MIXED METAL OXIDE CONTAINING SULFUR

FIELD OF THE INVENTION

The invention relates to a method of making Group 3 and Group 4 mixed metal oxide catalyst suitable for the decomposition of ethers to alkenes and alkanols. In an embodiment, it relates to a method of making a cerium-zirconium mixed metal oxide catalyst. In an embodiment, the catalyst made by the process of the invention is used for the production of isopropanol (IPA) from isopropyl ether (IPE).

BACKGROUND

The conversion of ethers to their corresponding alkenes and alkanols (aliphatic alcohols) is an important reaction in a number of commercial processes. This reaction is used, by way of example, to remove isopropyl ether (IPE) produced as the by-product of the hydration of propylene to produce isopropyl alcohol (IPA or isopropanol). In addition, an important route for the production of tertiary olefins involves reaction of mixed olefins with an alcohol over an acid catalyst to selectively produce a tertiary alkyl ether, separation of the ether from the remaining olefin stream, and then decomposition of the ether to the desired tertiary olefin. This latter process relies on the fact that tertiary olefins react with alcohols more rapidly than either secondary or primary olefins and hence provides an effective method for extracting tertiary olefins, such as isobutene and isoamylene, from a mixed olefin stream. For the purposes of this invention, a tertiary olefin or isoolefin will be understood to be an olefin containing at least one carbon atom that is covalently bonded to three other carbon atoms.

Various catalysts have been proposed for the selective decompostion of ethers. See for example U.S. Pat. No. 4,691,073, U.S. Pat. No. 4,254,290, U.S. Pat. Nos. 4,320,232 and 4,521,638, U.S. Pat. No. 4,398,051, U.S. Pat. No. 4,357,147. "Production D'Isobutene de Haute Puretépar Décomposition du MTBE" by P. B. Meunier et al. in Revue de L'Institut Francais du Petrole, vol. 46, No. 3, May 1991, pages 361 to 387, U.S. Pat. No. 5,254,785, U.S. Pat. No. 5,177,301, U.S. Pat. No. 5,171,920 and Japanese Published Patent Application No. JP-A-06072904.

Japanese Published Patent Application No. JP-A-59010528, published Jan. 20, 1984, describes a process for thermally decomposing a tertiary ether to a tertiary olefin in the presence of a titanium or zirconium oxide catalyst containing 0.1 to 20 wt % of $SO_4^{-2}$ groups. The catalyst activity is said to be high even at low temperatures thereby allowing co-production of the corresponding alcohol with negligible etherification.

U.S. Pat. No. 5,607,892 discloses a zirconium/cerium mixed oxide having a specific surface area of greater than 10 $m^2/g$. The mixed oxide is produced by intimately admixing a zirconium sol with a cerium sol, wherein the ratio of the mean diameter $r_1$ of the particles of the zirconium sol to the mean diameter $r_2$ of the particles of the cerium sol is at least 5, adding a precipitating amount of a base, such as aqueous ammonia, sodium hydroxide, or potassium hydroxide to the mixture, recovering the precipitate thus formed and calcining the precipitate at a temperature of 700 to 1,000° C. The mixed oxide is said to be useful as a catalyst or catalyst support for carrying out a variety of reactions, such as dehydration, hydrosulfurization, hydrodenitrification, desulfurization, hydrodesulfurization, dehydrohalogenation, reforming, steam reforming, cracking, hydrocracking, hydrogenation, dehydrogenation, isomerization, dismutation, oxychlorination, dehydrocyclization of hydrocarbons or other organic compounds, oxidation and/or reduction reactions, the Claus reaction, treatment of exhaust gases emanating from internal combustion engines, demetallation, methanation or shift conversion.

U.S. Pat. No. 6,150,299 discloses a cerium- and zirconium-based mixed oxide containing sulfur, which is said to be active as an exhaust gas purification catalyst and which comprises 50 to 79% by weight cerium oxide, 20 to 49% by weight zirconium oxide and 1 to 5% by weight sulfate ($SO_4$). In Example 1, the mixed oxide was produced by dispersing cerous sodium sulfate double salt (containing 75 g as cerium oxide) in 1,000 g of water and adding an aqueous solution of zirconium nitrate (containing 25 g as zirconium oxide). Then, an aqueous solution of sodium hydroxide was added until the pH of the mixture became 13.5, whereby a precipitate was obtained. This precipitate was separated from the mixture and heated in the air at 600° C. for 5 hours. Analysis showed the resultant mixed oxide to contain 73.9% by weight cerium oxide, 24.1% by weight zirconium oxide and 2.0% by weight sulfate.

International Patent Publication No. WO 03/37506, published May 8, 2003, discloses a promoter or catalyst support for an automobile exhaust gas system comprising a zirconium-cerium-based mixed oxide produced by reacting an alkali with an aqueous solution of a zirconium salt containing 0.42-0.7 mole of sulfate anion per mole of zirconium cation at a temperature not greater than 50° C. in the presence of a cerium salt to form a mixed cerium-zirconium hydroxide and then calcining the hydroxide at a temperature of 500 to 1000° C., such as 650 to 850° C.

U.S. Pat. No. 6,124,232 discloses a tungsten-modified zirconia catalyst produced by coprecipitating zirconia with an anion or oxyanion of tungsten in the presence of ammonium sulfate to obtain a sulfate-containing product, steaming the sulfate-containing product; recovering the sulfate-containing product by filtration, washing the product with water in order to remove the sulfate ions and calcining the product to produce a catalyst that is essentially free of sulfate ions. The catalyst is said to be active in the isomerization of paraffins.

U.S. Pat. No. 6,162,757 discloses a synthesis of a solid acid containing zirconium, in addition to a rare earth element, such as cerium, useful for isomerization of paraffins, ring opening of cyclics, hydrocracking, alkylation, hydrogenation of polynuclear aromatics, selective catalytic reduction of nitrogen peroxides, and oligomerization of light olefins.

U.S. Pat. No. 6,297,406 discloses a process for producing phenol and acetone from cumene hydroperoxide, in which cumene hydroperoxide is contact with a solid acid catalyst comprising a mixed oxide of cerium and a Group IVB metal.

Unpublished International Application No. PCT/US2004/041546 discloses a process for selectively converting a dialkyl ether to the corresponding alkene and alkanol, the process comprising contacting a feed containing at least one dialkyl ether with a catalyst comprising an acidic mixed metal oxide having the following composition:

$$X_m Y_n Z_p O_q$$

where X is at least one metal selected from Group 4 of the Periodic Table of Elements, Y is at least one metal selected from Group 3 (including the Lanthanides and Actinides) and Group 6 of the Periodic Table of Elements and Z is at least one metal selected from Groups 7, 8, and 11 of the Periodic Table of Elements; m, n, p and q are the atomic ratios of their respective components and, when m is 1, n is from 0.01 to 0.75, p is from 0 to 0.1, and q is the number of oxygen atoms necessary to satisfy the valence of the other components. The mixed oxides preferably contain sulfur, typically present in an amount of up to 5 wt %, such as up to 1 wt %, of the final mixed oxide composition. The mixed oxides can be prepared by impregnation or by co-precipitation from a liquid mixture containing a source of Group 4 metal ions and a source of Group 3 and/or Group 6 metal ions.

Ceria-zirconia catalysts and the like have also been found useful for the purification of exhaust gases, such as produced by an internal combustion engine. Such processes and catalyst made therefore have been described in, for instance, U.S. Pat. Nos. 5,478,543; 5,518,699; 5,532,198; 5,580,536; 5,582,785; 5,607,892; 5,712,218; 5,747,401; 5,908,800; 6,133,194; 6,150,299; 6,255,242; 6,291,719; 6,319,876; 6,506,705, and 6,605,565

The present invention provides an improved method of making Group 3 and Group 4 mixed metal oxides, particularly cerium-zirconium mixed metal oxides suitable for catalyzing the decomposition of ethers to alkenes and alkanols.

SUMMARY OF THE INVENTION

The invention is directed to a method of making an acidic mixed metal oxide having the composition expressed by the following formula (1):

$$X_m Y_n S_p O_q \tag{1}$$

wherein X is at least one metal selected from Group 4 of the Periodic Table of Elements, preferably zirconium, Y is at least one metal selected from Group 3 (including the Lanthanides and Actinides) of the Periodic Table of Elements, preferably cerium, S is sulfur, and O is oxygen; m, n, p and q are the atomic ratios of their respective components and, when m is 1, n is from about 0.01 to about 0.75, preferably from about 0.10 to about 0.35; p is 0.01 to about 0.50, preferably from about 0.10 to about 0.35; and q is the number of oxygen atoms necessary to satisfy the valence of the other components made by coprecipitating X and Y from separate salts in the presence of a sulfur-containing species, preferably in the form of sulfate ions. In a preferred embodiment, the sulfate ions are provided separately from the sources of the Group 3 and Group 4 metal-containing species used in the mixed oxide synthesis mixture, e.g., the sulfate ion is not the counter ion for the sources Group 3 and Group 4 metal-containing species. X and Y are preferably zirconium and cerium, respectively.

In a preferred embodiment, the invention is directed to a method of making a cerium-zirconium mixed oxide comprising coprecipitating cerium and zirconium from separate sources in the presence of sulfate ions. Advantageously, the sulfate ions are provided separately from the sources of cerium and zirconium used in the synthesis method, i.e., the sulfate ion is not the counter ion for cerium or zirconium species used as cerium and zirconium sources.

In yet a separate embodiment, the sources or Group 3 and Group 4 metal are salts, advantageously water-soluble salts.

The invention is also directed to a method of selectively converting a dialkyl ether to the corresponding alkene and alkanol comprising contacting a feed containing at least one dialkyl ether with a catalyst made according to the process of the present invention.

In a preferred embodiment, the invention is directed to a method of making IPA comprising contacting IPE with a ceria-zirconia catalyst in the presence of water, wherein said ceria-zirconia catalyst is made by a process comprising coprecipitating ceria and zirconia from separate cerium and zirconium sources in the presence of sulfate ions. In a preferred embodiment, the sulfate ions are provided separately from the cerium and zirconium sources, i.e., the sulfate ion is not the counter ion for cerium or zirconium species used as cerium and zirconium sources.

It is an object of the invention to provide an improved method of making a catalyst useful for the conversion of ethers to alkenes and alkanols.

These and other embodiments, objects, features, and advantages will become apparent as reference is made to the following detailed description, preferred embodiments, examples, and appended claims.

DETAILED DESCRIPTION

The invention is directed to an improved method of making a mixed metal oxide catalyst composition of the invention has the following empirical formula (1):

$$X_m Y_n S_p O_q \tag{1}$$

where X is at least one metal selected from Group 4 of the Periodic Table of Elements, preferably zirconium, Y is at least one metal selected from Group 3 (including the Lanthanides and Actinides) of the Periodic Table of Elements, preferably cerium, S is sulfur, and O is oxygen; m, n, p and q are the atomic ratios of their respective components and, when m is 1, n is from about 0.01 to about 0.75, preferably from about 0.10 to about 0.35; p is 0.01 to about 0.50, preferably from about 0.10 to about 0.35; and q is the number of oxygen atoms necessary to satisfy the valence of the other components made by coprecipitating X and Y from separate sources in the presence of a sulfur-containing species, preferably in the form of sulfate ions. In a preferred embodiment, the sulfate ions are provided separately from the sources of the Group 3 and Group 4 metal-containing species, e.g., the sulfate ion is not the counter ion for the Group 3 and Group 4 metal-containing species used in the mixed oxide synthesis mixture. X and Y are preferably zirconium and cerium, respectively. The Periodic Table of Elements referred to herein is the new notation described in Chemical and Engineering News 63(5), 27, 1985, which numbers the groups from 1 to 18.

Preferably, the sources of Group 3 and Group 4 metals are salts, advantageously water-soluble salts.

Suitable Group 4 metals include titanium, zirconium and hafnium, with zirconium being most preferred. Suitable Group 3 metals include scandium, yttrium and lanthanum, and metals from the Lanthanide or Actinide series, such as cerium, praseodymium, neodymium, samarium, europium, gadolinium, terbium, dysprosium, holmium, erbium, thulium, ytterbium, lutetium and thorium. The most preferred Group 3 metal is cerium.

The invention is also directed to the mixed metal oxide in formula (1) made by a process of coprecipitating X and Y from separate sources in the presence of sulfur (S) ions.

The process according to the present invention comprises co-precipitation of X and Y in formula (1) from a liquid mixture in the presence of a source of sulfur, preferably in the form of sulfate ions. X and Y are provided by as separate sources, such as salts, each preferably highly soluble in the solution, which is preferably an aqueous solution. The slurry comprising the coprecipitate is optionally aged by, for instance, storage in a steambox or autoclave, preferably with agitation, for a predetermined period of time, such as from about 4 or 5 hours to about 200 hours, preferably from about 12 to about 100 hours, more preferably from about 20 hours to about 150 hours, still more preferably from about 24 hours to about 72 hours, and at a predetermined temperature, such as between about 50 and 250° C., or preferably about 50 to about 200° C., or more preferably about 75 to about 150° C. The coprecipitate may be conveniently recovered by filtration, followed by drying and then calcination of the resulting catalyst precursor in the manner described below.

The liquid mixture can be prepared by combining a first liquid solution comprising a source of Group 4 metal ions with a second liquid solution comprising a source of Group 3 metal ions, wherein the combination takes place under conditions sufficient to cause co-precipitation of the catalyst precursor as a solid from the liquid medium. It is preferred that the two solutions be combined by nozzle mixing as is per se known in the art. Alternatively, the source of the Group 4 metal ions and the source of the Group 3 metal ions may be combined into a single solution. This solution may then be subjected to conditions sufficient to cause co-precipitation of the catalyst, such as by the addition of a precipitating reagent, such as ammonium hydroxide and the like, to the solution. In a preferred embodiment, an aqueous solution of a base is added so that the pH of the solution containing X, Y, and S is caused to be about greater than 7 to at or below 9, preferably about 8.

Suitable sources of the metal ions for the coprecipitation include compounds such as oxychlorides, chlorides, alkoxides, sulfates and nitrates. In one embodiment, at least one of the metals is present as a sulfate. Preferably, a separate source of sulfate ions is added to the liquid mixture from which the catalyst precursor is precipitated. Suitable separate sources of sulfate ion include sulfuric acid, ammonium sulfate, sodium sulfate, cerium sulfate, zirconium sulfate, and mixtures thereof.

Where the Group 4 metal includes zirconium, the preferred source of zirconium is zirconyl nitrate.

Where the Group 3 metal includes cerium, the preferred source of cerium is a cerium sulfate-sulfuric acid complex or more preferably cerium nitrate.

Calcination of the catalyst precursor is effected, typically in an oxidizing atmosphere, at a temperature of at least 400° C., such as at least 500° C., for example from about 500° C. to about 800° C. The calcination time may be up to 48 hours, such as for about 0.5 to about 24 hours, for example for about 1 to about 10 hours. Where the catalyst precursor contains sulfate ions, the calcination conditions should be controlled so as to retain the desired sulfur level in the final catalyst composition.

The method of making a mixed metal oxide of the present invention provides several advantages over known methods. Non limiting examples of such advantages include: the method produces very high yields per batch of mixed oxide of formula (1); the method allows to produce catalysts with excellent catalytic performance.

The mixed oxides prepared by the method of the present invention are useful catalysts for the decomposition of ethers. The ether decomposition process of the invention involves contacting an ether-containing feed with a mixed metal oxide catalyst described above under conditions effective to convert the ether to an olefin and an alcohol. Suitable ethers for use in the process of the invention include those having the formula:

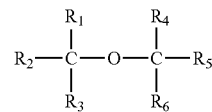

wherein $R_1$, $R_2$, $R_3$, $R_4$, $R_5$ and $R_6$ are the same or different and are selected from hydrogen, alkyl, arylalkyl and alkylaryl species, each preferably having up to 20 carbon atoms, with the proviso that when all the substituents $R_1$ through $R_6$ are hydrogen (i.e., the compound is dimethyl ether), the product is principally methanol.

In general, the conditions employed are not narrowly defined and depend not only on the ether starting material but also on the desired conversion rate and product selectivity. Typically, however, the conditions will include a temperature of about 50° C. to about 320° C., a pressure of about 0 $kPa_g$ (gauge pressure) to about 3500 $kPa_g$, and a weight hourly space velocity (WHSV) of about 0.1 $hr^{-1}$ to about 25 $hr^{-1}$; such as a temperature of about 100° C. to about 275° C., a pressure of about 0 $kPa_g$ to about 2400 $kPa_g$ and a weight hourly space velocity (WHSV) of about 0.5 $hr^{-1}$ to about 10 $hr^{-1}$.

In one practical embodiment, the ether-containing feed contains methyl tert-butyl ether (MTBE) and is produced by reacting a mixed butene stream with methanol. After separation, the present process is used to selectively decompose the resultant MTBE to iso-butene and methanol. A similar process can be used with mixed pentenes to produce tert-amyl methyl ether (TAME) for selective conversion to isoamylene and methanol. In this embodiment, suitable ether decomposition conditions include a temperature of about 100° C. to about 200° C. and a pressure of about 0 $kPa_g$ to about 1000 $kPa_g$ and a weight hourly space velocity (WHSV) of about 1 $hr^{-1}$ to about 10 $hr^{-1}$.

In yet another practical embodiment, the ether-containing feed contains sec-butyl ether (SBE) and is produced as a by-product of the hydration of butene to produce sec-butanol. One possible method of disposal of the SBE is as a fuel, for example by addition to motor vehicle gasoline, but, not only may this be subject to environmental regulation, it also leads to a loss of butenes as a lower-valued component. Moreover, the SBE may not be readily isolatable as a single component stream by conventional separation techniques, and may form a mixture with close-boiling butene oligomers composed mostly of $C_8$ olefins formed by dimerization of the butenes. However, while the $C_8$ olefins, being highly branched, would make a good high-octane additive to gasoline, environmental regulation may require elimination of the SBE from this stream. Accordingly, a preferred decomposition pathway for SBE is by conversion to sec-butanol and 2-butene in a process that limits oligomerization of the butene formed and of the $C_8$ olefins present.

The catalyst compositions of the present invention are active for the selective conversion of SBE to sec-butanol and 2-butene with limited oligomerization of the resultant butenes and limited oligomerization/isomerization of any $C_8$ olefins present. At higher temperatures, some or all of the sec-butanol may be dehydrated to 2-butene according to a reaction of the type indicated above as reaction (2). In this embodiment, preferred ether decomposition conditions include a temperature of about 150° C. to about 275° C., a pressure of about 0 kPa$_g$ to about 700 kPa$_g$, and a weight hourly space velocity (WHSV) of about 0.5 hr$^{-1}$ to about 10 hr$^{-1}$. Conveniently, the feed to the catalyst includes water in addition to the SBE, with the molar ratio of water to SBE typically ranging from 0 to 3, such as about 0.5 to about 2, for example about 1.5.

In another embodiment, the catalyst made by the process of the invention may be used for the purification of exhaust gases produced by an internal combustion engine, e.g., for use in catalytic converters, by contacting such a gas with the catalyst according to the present invention.

In a preferred embodiment, the ether-containing feed contains isopropyl ether (IPE). In a more preferred embodiment the IPE is produced as a by-product of propylene hydration, in a process for the manufacture of isopropyl alcohol (IPA). Some IPA processes involve contacting propylene with sulfuric acid. This can be accomplished with gas/liquid absorption or liquid/liquid extraction. While these processes have been utilized for several decades, some improvements have been made. The improvements include a process configuration that utilizes a unique combination of plug flow, bubble column, and closed stirred tank reactor reaction sections to achieve high conversion of dilute or concentrated propylene. Also spargers custom designed for the propylene/sulfuric acid absorption/extraction section can be used. Further, loop reactors may be preferred to improve mixing integrity.

One possible method of disposal of IPE produced as a side-product of EPA is as a fuel but, not only may this be subject to environmental regulation, but also a higher economic value can be achieved by selective decomposition of the IPE to propylene and IPA. The optimal pathway for this reaction is therefore shown by reaction (1):

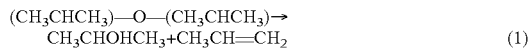
$$(CH_3CHCH_3)-O-(CH_3CHCH_3) \rightarrow CH_3CHOHCH_3 + CH_3CH=CH_2 \qquad (1)$$

The challenge faced in the catalytic decomposition of IPE is two-fold, firstly, minimizing the dehydration of IPA formed by reaction (1) to propylene according the reaction (2):

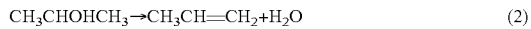
$$CH_3CHOHCH_3 \rightarrow CH_3CH=CH_2 + H_2O \qquad (2)$$

and secondly, minimizing oligomerization of the propylene formed according to reaction (3):

$$xCH_3CH=CH_2 \rightarrow (C_3H_6)_x \qquad (3)$$

Although each of reactions (1)-(3) is acid catalyzed, the process of the invention is effective to decompose IPE according to reaction (1) while reducing EPA dehydration and propylene oligomerization. Preferably, the conditions used to effect IPE decomposition include a temperature of about 100° C. to about 320° C., such as about 200° C. to about 300° C., for example about 240° C. to about 280° C.; a pressure of about 100 kPa$_g$ to about 3550 kPa$_g$, such as about 400 kPa$_g$ to about 1800 kPa$_g$, for example about 700 kPa$_g$ to about 1500 kPa$_g$, a weight hourly space velocity (WHSV) of about 0.5 hr$^{-1}$ to about 10 hr$^{-1}$, such as about 3 hr$^{-1}$ to about 10 hr$^{-1}$, for example about 7 hr$^{-1}$. Conveniently, the feed to the catalyst includes water in addition to the IPE, with the molar ratio of water to IPE typically ranging from 0 to 3, such as about 0.5 to about 2, for example about 1.5.

The processes of the invention may be conducted in a stationary or fluidized bed, and may take place continuously or batch-wise.

The processes of the invention may be conducted using pure ether feedstocks, or they may include a diluent such as nitrogen, argon, carbon dioxide, alkanes, and the like. In a preferred embodiment, water may be added together with the ether feed to minimize dehydration of the resultant alcohols.

The mixed oxides made by the method of the present invention may also be used as catalysts in other processes, such as for producing phenol and acetone from cumene hydroperoxide, for isomerization of paraffins, ring opening of cyclics, hydrocracking, alkylation, hydrogenation of polynuclear aromatics, selective catalytic reduction of nitrogen oxides, oligomerization of light olefins, dehydrogenation of ethylbenzene to styrene and methanation, and oxidation-reduction reactions. In a preferred embodiment, the mixed oxides prepared by the method of the present invention may be used as catalysts or catalyst supports in the treatment of exhaust gases.

EXPERIMENTAL

The following examples are meant to illustrate the present invention and provide a comparison with other methods. Numerous modifications and variations are possible and it is to be understood that within the scope of the appended claims, the invention may be practiced otherwise than as specifically described herein.

Examples 1 through 11 describe the synthesis of ceria/zirconia catalyst.

Example 1

Ce(III) Nitrate Impregnated on ZrO2

A solution was prepared by adding 3.10 grams of cerium (III) nitrate hexahydrate to 10 grams of distilled water. This solution was added slowly and drop-wise to 10 grams of zirconium hydroxide obtained from MEI Corporation. The catalyst was dried at 100° C. overnight and then calcined in flowing air at 500° C. for three hours. The elemental analyses are shown in Table 1, below.

Example 2

Ce(IV) Sulfate Impregnated on ZrO2

A solution was prepared by adding 2.40 grams of cerium (IV) sulfate to 10 grams of distilled water. This solution was added slowly and drop-wise to 10 grams of zirconium hydroxide obtained from MEI Corporation. The catalyst was dried at 100° C. overnight and then calcined in flowing air at 500° C. for three hours. The elemental analyses are shown in Table 1.

Example 3

Ce(III) Nitrate Co-Precipitated with Zirconyl Chloride

Ninety grams of ZrO(NO$_3$)$_2$.xH$_2$O and 25 grams of cerium (II) nitrate hexahydrate were dissolved with stirring in 1.5 liters of distilled water. A second solution containing 65 grams of concentrated NH$_4$OH and 1.5 liters of distill water was prepared. These two solutions were combined at the rate of 50 ml/min using a nozzle mixing. The pH of the final composite was adjusted to approximately 8 by the addition of concentrated ammonium hydroxide. This slurry having a solids content of about 2-3 wt % was then put in polypropylene bottles and placed in a steambox (100° C.) for 72 hours. The product formed was recovered by filtration, washed with excess water, and stored as a filtercake. The filtercake is dried overnight at 250° F. Thereafter the filtercake is calcined at 700° C. for a total of 3 hours in flowing air and then allowed to cool. The elemental analyses are shown in Table 1.

Example 4

Ce(IV) Sulfate Co-Precipitated with Zirconyl Chloride

One hundred and twenty-five grams of $ZrOCl_2.8H_2O$ and 19 grams of $Ce(SO_4)_2$ were dissolved with stirring in 1.5 liters of distilled water. A second solution containing 65 grams of concentrated $NH_4OH$ and 1.5 liters of distill water was prepared. These two solutions were combined at the rate of 50 ml/min using a nozzle mixing. The pH of the final composite was adjusted to approximately 8 by the addition of concentrated ammonium hydroxide. This slurry having a solids content of about 3 wt % was then put in polypropylene bottles and placed in a steambox (100° C.) for 72 hours. The product formed was recovered by filtration, washed with excess water, and stored as a filtercake. The filtercake is dried overnight at 100° C. Thereafter the filtercake is calcined at 700° C. for a total of 3 hours in flowing air and then allowed to cool. The elemental analyses are shown in Table 1.

Example 5

Ce(IV) Sulfate Co-Precipitated with Zirconyl Nitrate

Ninety grams of $ZrO(NO_3)_2.xH_2O$ and 19 grams of $Ce(SO_4)_2$ were dissolved with stirring in 1.5 liters of distilled water. A second solution containing 65 grams of concentrated $NH_4OH$ and 1.5 liters of distill water was prepared. These two solutions were combined at the rate of 50 ml/min using a nozzle mixing. The pH of the final composite was adjusted to approximately 8 by the addition of concentrated ammonium hydroxide. This slurry having a solids content of 3 wt % was then put in polypropylene bottles and placed in a steambox (100° C.) for 72 hours. The product formed was recovered by filtration, washed with excess water, and stored as a filtercake. The filtercake is dried overnight at 100° C. Thereafter the filtercake is calcined at 700° C. for a total of 3 hours in flowing air and then allowed to cool. The elemental analyses are shown in Table 1.

Example 6

Ce(IV) Sulfate Hydrate—Sulfuric Acid Complex Co-Precipitated with Zirconyl Chloride Five hundred and sixty-three grams of $ZrOCl_2.xH_2O$ and 95 grams of cerium sulfate hydrate-sulfuric acid complex [CAS#17106-39-7] were dissolved with stirring in 1.5 liters of distilled water. A second solution containing 130 grams of concentrated $NH_4OH$ and 1.5 liters of distill water was prepared. These two solutions were combined at the rate of 50 ml/min using a nozzle mixing. The pH of the final composite was adjusted to approximately 8 by the addition of concentrated ammonium hydroxide. This slurry having a solids content of about 7 wt % was then put in polypropylene bottles and placed in a steambox (100° C.) for 72 hours. The product formed was recovered by filtration, washed with excess water, and stored as a filtercake. The filtercake is dried overnight at 100° C. Thereafter the filtercake is calcined at 700° C. for a total of 3 hours in flowing air and then allowed to cool. The elemental analyses are shown in Table 1.

Example 7

Ce(IV) Sulfate Hydrate—Sulfuric Acid Co-Precipitated with Zirconyl Nitrate

Four hundred and five grams of $ZrO(NO_3)_2.xH_2O$ and 95 grams of cerium sulfate hydrate-sulfuric acid complex [CAS#17106-39-7] were dissolved with stirring in 1.5 liters of distilled water. Another solution containing 130 grams of concentrated $NH_4OH$ and 1.5 liters of distill water was prepared. These two solutions were combined at the rate of 50 ml/min using a nozzle mixing. The pH of the final composite was adjusted to approximately 8 by the addition of concentrated ammonium hydroxide. This slurry having a solids content of about 7 wt % was then divided into four equal portions and labeled A through D. Approximately one hour later, sample A was recovered by filtration, washed with excess water, and stored as a filtercake. Sample B was allowed to stir at room temperature overnight and then recovered by filtration, washed with excess water, and stored as a filtercake. Sample C was put in polypropylene bottle and placed in a steambox (100° C.) for 24 hours, then recovered by filtration, washed with excess water, and stored as a filtercake. Sample D was put in polypropylene bottle and placed in a steambox (100° C.) for 72 hours, then recovered by filtration, washed with excess water, and stored as a filtercake. The filtercakes from products A through D were dried overnight at 100° C. Thereafter the filtercakes were calcined at 700° C. for a total of 3 hours in flowing air and then allowed to cool. The elemental analyses are shown in Table 1.

Example 8

Ce(III) Sulfate Co-Precipitated with Zirconyl Nitrate

One hundred and thirty one grams of $ZrO(NO_3)_2.xH_2O$ and 28.4 grams of $Ce_2(SO_4)_3$ were dissolved with stirring in 528 grams of distilled water. A second solution containing 65.9 grams of concentrated $NH_4OH$ and 366.9 grams of distilled water was prepared. These two solutions were combined at the rate of 50 ml/min using a nozzle mixing. The pH of the final composite was adjusted to approximately 8 by the addition of concentrated ammonium hydroxide. This slurry having a solids content of about 7%, was then aged in an autoclave at 100° C. for 72 hours. The product formed was recovered by filtration, washed with excess water, and stored as a filtercake. The filtercake was dried overnight at 120° C. Thereafter, the filtercake was calcined at 700° C. for a total of 3 hours in flowing air and then allowed to cool. The elemental analyses are shown in Table 1.

Example 9

Ce(IV) Nitrate Co-Precipitated with Zirconyl Nitrate in Presence of Sulfuric Acid One hundred and thirty one grams of $ZrO(NO_3)_2.xH_2O$, 72.9 grams of $Ce(NO_3)_4$, and 17 grams of concentrated $H_2SO_4$ were dissolved with stirring in 466 grams of distilled water. A second solution containing 94.8 grams of concentrated $NH_4OH$ and 528 grams of distilled water was prepared. These two solutions were combined at the rate of 50 ml/min using a nozzle mixing. The pH of the final composite was adjusted to approximately 8 by the addition of concentrated ammonium hydroxide. This slurry, having a solids content of about 7%, and was then aged in an autoclave at 100° C. for 72 hours. The product formed was recovered by filtration, washed with excess water, and stored as a filtercake. The filtercake was dried overnight at 120° C. Thereafter, the filtercake was calcined at 700° C. for a total of 3 hours in flowing air and then allowed to cool. The elemental analyses are shown in Table 1.

washed with excess water, and stored as a filtercake. The filtercake was dried overnight at 120° C. Thereafter, the filtercake was calcined at 700° C. for a total of 3 hours in flowing air and then allowed to cool. The elemental analyses are shown in Table 1.

TABLE 1

Elemental Analyses of Examples 1-11

| Example | Cerium % | Zirconium % | Sulfur % | Cerium moles | Zirconium moles | Sulfur moles | Ce n | Zr m | S P |
|---|---|---|---|---|---|---|---|---|---|
| 1 | 11.40 | 60.87 | 0.10 | 0.08 | 0.67 | 0.01 | 0.12 | 1.00 | 0.01 |
| 2 | 7.89 | 58.48 | 3.04 | 0.06 | 0.64 | 0.19 | 0.09 | 1.00 | 0.30 |
| 3 | 17.80 | 54.15 | 0.15 | 0.13 | 0.60 | 0.01 | 0.21 | 1.00 | 0.02 |
| 4 | 13.10 | 57.02 | 1.10 | 0.09 | 0.63 | 0.07 | 0.15 | 1.00 | 0.11 |
| 5 | 18.80 | 50.81 | 0.52 | 0.13 | 0.56 | 0.03 | 0.24 | 1.00 | 0.06 |
| 6 | 12.00 | 56.95 | 1.10 | 0.09 | 0.63 | 0.07 | 0.14 | 1.00 | 0.11 |
| 7a | 15.00 | 55.07 | 1.10 | 0.11 | 0.61 | 0.07 | 0.18 | 1.00 | 0.11 |
| 7b | 14.90 | 53.26 | 2.20 | 0.11 | 0.59 | 0.14 | 0.18 | 1.00 | 0.23 |
| 7c | 14.30 | 53.83 | 0.88 | 0.10 | 0.59 | 0.06 | 0.17 | 1.00 | 0.09 |
| 7d | 14.90 | 55.48 | 0.97 | 0.11 | 0.61 | 0.06 | 0.17 | 1.00 | 0.10 |
| 8 | 17.30 | 51.40 | 2.00 | 0.12 | 0.56 | 0.13 | 0.22 | 1.00 | 0.22 |
| 9 | 18.00 | 52.80 | 1.10 | 0.13 | 0.58 | 0.07 | 0.22 | 1.00 | 0.12 |
| 10 | 17.20 | 49.90 | 1.70 | 0.12 | 0.55 | 0.11 | 0.22 | 1.00 | 0.19 |
| 11 | 18.20 | 51.20 | 1.00 | 0.13 | 0.56 | 0.06 | 0.23 | 1.00 | 0.11 |
| 23 | 11.50 | 59.95 | 0.07 | 0.08 | 0.66 | 0.00 | 0.12 | 1.00 | 0.01 |
| 24 | 14.20 | 57.46 | 0.05 | 0.10 | 0.63 | 0.00 | 0.16 | 1.00 | 0.01 |

Example 10

Ce(III) Nitrate Co-Precipitated with Zirconyl Nitrate in Presence of Sulfuric Acid One hundred and thirty one grams of $ZrO(NO_3)_2 \cdot xH_2O$, 36.1 grams of $Ce(NO_3)_3$, and 17 grams of concentrated $H_2SO_4$ were dissolved with stirring in 511 grams of distilled water. A second solution containing 76.5 grams of concentrated $NH_4OH$ and 426 grams of distilled water was prepared. These two solutions were combined at the rate of 50 ml/min using a nozzle mixing. The pH of the final composite was adjusted to approximately 8 by the addition of concentrated ammonium hydroxide. This slurry having a solids content of about 7%, was then aged in an autoclave at 100° C. for 72 hours. The product formed was recovered by filtration, washed with excess water, and stored as a filtercake. The filtercake was dried overnight at 120° C. Thereafter, the filtercake was calcined at 700° C. for a total of 3 hours in flowing air and then allowed to cool. The elemental analyses are shown in Table 1.

Example 11

Ce(IV) Nitrate Co-Precipitated with Zirconyl Nitrate in Presence of Sulfuric Acid Using High Solids Preparation Two hundred and sixty two grams of $ZrO(NO_3)_2 \cdot xH_2O$, 145.8 grams of $Ce(NO_3)_4$, and 34 grams of concentrated $H_2SO_4$ were dissolved with stirring in 466 grams of distilled water. A second solution containing 189.6 grams of concentrated $NH_4OH$ and 528 grams of distilled water was prepared. These two solutions were combined at the rate of 50 ml/min using a nozzle mixing. The pH of the final composite was adjusted to approximately 8 by the addition of concentrated ammonium hydroxide. This slurry having a solids content of about 14%, was then aged in an autoclave at 100° C. for 72 hours. The product formed was recovered by filtration, Examples 12 through 24 describe IPE decomposition over the catalysts prepared above and two commercially available catalysts.

Example 12

IPE Decomposition Over Ce(III) Nitrate Impregnated on ZrO2

The decomposition of IPE was investigated in a fixed-bed microreactor. 0.5 grams of the catalyst of Example 1 were loaded into a ⅜" O.D. stainless steel reactor and dried with $N_2$ at 210° C. A sample of isopropyl ether (IPE) from the Baton Rouge Chemical Plant (approximately 95 wt % IPE) was fed to the reactor at a WHSV of 5 h$^{-1}$. In addition, HPLC grade water was co-fed to the reactor at an IPE:$H_2O$ molar ratio of 1:1. Reactor temperature was 210° C. and pressure was 90 psig. IPE conversion is defined as $(IPE_{product}-IPE_{feed})/IPE_{feed}$, and IPA selectivity is defined as $IPA_{product}/$(Theoretical IPA produced from IPE decomposed). IPA Yield (Per Pass) is defined as the product of the IPE Conversion and the IPA Selectivity. Note: "Theoretical IPA produced" is the number of moles of IPA that are formed when a mole of IPE decomposes via reaction (1) above. Thus, if one mole of IPE decomposes to form 1 mole of IPA and 1 mole of propylene, then the IPA selectivity would be equal to 100%. If less than one mole of IPA is produced, e.g., due to subsequent dehydration of the IPA to propylene, then IPA selectivity would be less than 100%. If additional IPA is formed, e.g, by hydration of the propylene formed back to IPA, then IPA selectivity could be greater than 100%.

The reactor was run for 24 hours. IPE conversion was <1% throughout, and IPA yields were approximately zero. The data show that the Ce(III) nitrate impregnated on zirconia was inactive for IPE decomposition.

Example 13

IPE Decomposition over Ce(IV) Sulfate Impregnated on ZrO2

The decomposition of IPE was investigated in a fixed-bed microreactor. 0.5 grams of the catalyst of Example 2 were loaded into a ⅜" O.D. stainless steel reactor and dried with $N_2$ at 210° C. The same grade sample of isopropyl ether (IPE) from the Baton Rouge Chemical Plant as in Example 12 was fed to the reactor at a WHSV of 5 $h^{-1}$. In addition, HPLC grade water was co-fed to the reactor at an IPE:$H_2O$ molar ratio of 1:1. Reactor temperature was 210° C. and pressure was 90 psig. The data for IPE conversion and IPA yields are shown in Table 2.

TABLE 2

Decomposition of IPE over Ce(IV) sulfate impregnated on $ZrO_2$

| Composition (wt. %) | Feed | Product Time on Stream (hrs) | |
|---|---|---|---|
| | | 20 | 50 |
| Propylene | 1.13 | 8.35 | 2.93 |
| Isopropanol (IPA) | 1.29 | 9.63 | 4.67 |
| Isopropyl Ether (IPE) | 82.42 | 63.39 | 74.40 |
| IPE Conversion (%) | | 23.1 | 9.7 |
| IPA Selectivity (%) | | 74.6 | 71.8 |
| IPA Yield (Per Pass) (%) | | 17.2 | 7.0 |

As the data in Table 2 show, the catalyst shows some activity for IPE decomposition. The catalyst is, however, not stable, and activity for IPE decomposition decreases rapidly with time. Comparing Example 13 with Example 12 shows, however, that the catalyst prepared by impregnation of Ce(IV) sulfate salt on zirconia has higher activity than the catalyst prepared by impregnation of the Ce(III) nitrate salt on zirconia.

Example 14

IPE Decomposition over Ce(III) Nitrate Co-Precipitated with Zirconyl Chloride The decomposition of IPE was investigated in a fixed-bed microreactor. 0.5 grams of the catalyst of Example 3 were loaded into a ⅜" O.D. stainless steel reactor and dried with $N_2$ at 210° C. A sample of isopropyl ether (IPE) from the Baton Rouge Chemical Plant (same grade as in Example 12) was fed to the reactor at a WHSV of 5 $h^{-1}$. In addition, HPLC grade water was co-fed to the reactor at an IPE:$H_2O$ molar ratio of 1:1. Reactor temperature was 210° C. and pressure was 90 psig.

The reactor was run for 24 hours. IPE conversion was <2% throughout, and IPA yields were approximately zero, showing that the Ce(III)/$ZrO_2$ catalyst prepared by co-precipitation was inactive for IPE decomposition.

Example 15

IPE Decomposition Over Ce(IV) Sulfate Co-Precipitated with Zirconyl Chloride The decomposition of IPE was investigated in a fixed-bed microreactor. 0.5 grams of the catalyst of Example 4 were loaded into a ⅜" O.D. stainless steel reactor and dried with $N_2$ at 210° C. A sample of isopropyl ether (IPE) from the Baton Rouge Chemical Plant (same grade as in Example 12) was fed to the reactor at a WHSV of 5 $h^{-1}$. In addition, HPLC grade water was co-fed to the reactor at an IPE:$H_2O$ molar ratio of 1:1. Reactor temperature was 210° C. and pressure was 90 psig. The data for IPE conversion and IPA yields are shown in Table 3.

TABLE 3

Decomposition of IPE over Ce(IV) sulfate co-precipitated with zirconyl chloride

| Composition (wt. %) | Feed | Product Time on Stream (hrs) | |
|---|---|---|---|
| | | 50 | 65 |
| Propylene | 1.13 | 17.97 | 13.43 |
| Isopropanol (IPA) | 1.29 | 23.31 | 22.10 |
| Isopropyl Ether (IPE) | 82.42 | 43.76 | 50.28 |
| IPE Conversion (%) | | 47.0 | 39.1 |
| IPA Selectivity (%) | | 96.4 | 109.5 |
| IPA Yield (Per Pass) (%) | | 45.3 | 42.8 |

As the data in Table 3 show, the catalyst shows significant activity for IPE decomposition. Comparing Example 15 with Example 13 shows that the catalyst prepared via co-precipitation with the Ce(IV) sulfate salt has significantly higher activity than the catalyst prepared via impregnation using the same cerium salt.

Example 16

IPE Decomposition Over Ce(IV) Sulfate Co-Precipitated with Zirconyl Nitrate The decomposition of IPE was investigated in a fixed-bed microreactor. 0.5 grams of the catalyst of Example 5 were loaded into a ⅜" O.D. stainless steel reactor and dried with $N_2$ at 210° C. A sample of isopropyl ether (IPE) from the Baton Rouge Chemical Plant (same grade as in Example 12) was fed to the reactor at a WHSV of 5 $h^{-1}$. In addition, HPLC grade water was co-fed to the reactor at an IPE:$H_2O$ molar ratio of 1:1. Reactor temperature was 210° C. and pressure was 90 psig. The data for IPE conversion and IPA yields are shown in Table 4.

TABLE 4

Decomposition of IPE over Ce(IV) sulfate co-precipitated with zirconyl nitrate

| Composition (wt. %) | Feed | Product Time on Stream (hrs) | |
|---|---|---|---|
| | | 50 | 65 |
| Propylene | 1.13 | 16.51 | 15.76 |
| Isopropanol (IPA) | 1.29 | 27.32 | 26.34 |
| Isopropyl Ether (IPE) | 82.42 | 40.86 | 42.53 |
| IPE Conversion (%) | | 50.4 | 48.4 |
| IPA Selectivity (%) | | 108.8 | 109.3 |
| IPA Yield (Per Pass) (%) | | 54.9 | 52.9 |

As the data in Table 4 show, the catalyst shows significant activity for IPE decomposition. Comparing Example 16 with Example 15 shows that the catalyst prepared via co-precipitation with the zirconyl nitrate salt has improved performance over the catalyst prepared via co-precipitation with the zirconyl chloride salt.

Example 17

IPE Decomposition Over Ce(IV) Sulfate Hydrate—Sulfuric Acid Complex Co-Precipitated with Zirconyl Chloride The decomposition of IPE was investigated in a fixed-bed microreactor. 0.5 grams of the catalyst of Example 6 were loaded into a ⅜" O.D. stainless steel reactor and dried with $N_2$ at 210° C. A sample of isopropyl ether (IPE) from the Baton Rouge Chemical Plant (same grade as in Example 12) was fed to the reactor at a WHSV of 5 $h^{-1}$. In addition, HPLC grade water was co-fed to the reactor at an IPE:$H_2O$ molar ratio of 1:1. Reactor temperature was 210° C. and pressure was 90 psig. The data for IPE conversion and IPA yields are shown in Table 5.

TABLE 5

Decomposition of IPE over 10% Ce(IV) sulfate sulfuric acid complex co-precipitated with zirconyl chloride

|  |  | Product Time on Stream (hrs) | |
|---|---|---|---|
| Composition (wt. %) | Feed | 50 | 70 |
| Propylene | 1.13 | 12.73 | 12.07 |
| Isopropanol (IPA) | 1.29 | 23.10 | 21.27 |
| Isopropyl Ether (IPE) | 82.42 | 48.73 | 51.15 |
| IPE Conversion (%) |  | 40.9 | 37.9 |
| IPA Selectivity (%) |  | 110.2 | 108.7 |
| IPA Yield (Per Pass) (%) |  | 45.0 | 41.2 |

As the data in Table 5 show, the catalyst shows significant activity for IPE decomposition. These data show that the Ce(IV) sulfate hydrate—sulfuric acid complex is a suitable precursor for the preparation of the ceria-zirconia catalyst.

Example 18

IPE Decomposition Over Ce(IV) Sulfate Hydrate—Sulfuric Acid Co-Precipitated with Zirconyl Nitrate—Effect of Gel Aging The decomposition of IPE was investigated in a fixed-bed microreactor. 0.5 grams each of catalyst sample A, C and D from Example 7 were loaded into a ⅜" O.D. stainless steel reactor and dried with $N_2$ at 210° C. A sample of isopropyl ether (IPE) from the Baton Rouge Chemical Plant (same grade as in Example 12) was fed to the reactor at a WHSV of 5 $h^{-1}$. In addition, HPLC grade water was co-fed to the reactor at an IPE:$H_2O$ molar ratio of 1:1. Reactor temperature was 210° C. and pressure was 90 psig. The data for IPE conversion and IPA yields taken at 15 hours time-on-stream for each sample tested are shown in Table 6.

TABLE 6

Decomposition of IPE over Ce(IV) sulfate co-precipitated with zirconyl nitrate

|  |  | Product Catalyst Sample | | |
|---|---|---|---|---|
| Composition (wt. %) | Feed | A | C | D |
| Propylene | 1.13 | 22.17 | 11.66 | 12.68 |
| Isopropanol (IPA) | 1.29 | 20.86 | 21.44 | 22.40 |
| Isopropyl Ether (IPE) | 82.42 | 39.98 | 52.15 | 50.21 |
| IPE Conversion (%) |  | 51.5 | 36.7 | 39.1 |
| IPA Selectivity (%) |  | 78.5 | 113.2 | 111.5 |
| IPA Yield (Per Pass) (%) |  | 40.4 | 41.6 | 43.6 |

The data of Table 6 show that gel aging has an effect on the performance of the catalyst. The aging of the gel at elevated temperatures and for longer duration increases the IPA yield.

Example 19

IPE Decomposition Over Ce(III) Sulfate Co-Precipitated with Zirconyl Nitrate The decomposition of IPE was investigated in a fixed-bed microreactor. 0.5 grams of the catalyst of Example 8 were loaded into a ⅜" O.D. stainless steel reactor and dried with $N_2$ at 210° C. A sample of isopropyl ether (IPE) from the Baton Rouge Chemical Plant (same grade as in Example 12) was fed to the reactor at a WHSV of 5 $h^{-1}$. In addition, HPLC grade water was co-fed to the reactor at an IPE:$H_2O$ molar ratio of 1:1. Reactor temperature was 210° C. and pressure was 90 psig. The data for IPE conversion and IPA yields are shown in Table 7.

As the data in Table 7 show, the catalyst shows significant activity for IPE decomposition, demonstrating that the Ce(III) sulfate is a suitable precursor for the preparation of the ceria-zirconia catalyst.

Example 20

IPE Decomposition Over Ce(IV) Nitrate Co-Precipitated with Zirconyl Nitrate in Presence of Sulfuric Acid The decomposition of IPE was investigated in a fixed-bed microreactor. 0.5 grams of the catalyst of Example 9 were loaded into a ⅜" O.D. stainless steel reactor and dried with $N_2$ at 210° C. A sample of isopropyl ether (IPE) from the Baton Rouge Chemical Plant (same grade as in Example 12) was fed to the reactor at a WHSV of 5 $h^{-1}$. In addition, HPLC grade water was co-fed to the reactor at an IPE:$H_2O$ molar ratio of 1:0.8. Reactor temperature was 210° C. and pressure was 90 psig. The data for IPE conversion and IPA yields are shown in Table 8, demonstrating that a catalyst prepared using separate sources of cerium(IV), zirconium, and sulfate species has significant activity for IPE conversion to IPA.

TABLE 8

Decomposition of IPE over Ce(IV) nitrate co-precipitated with zirconyl nitrate in presence of $H_2SO_4$

|  |  | Product Time on Stream (hrs) | |
|---|---|---|---|
| Composition (wt. %) | Feed | 50 | 65 |
| Propylene | 1.13 | 18.89 | 15.80 |
| Isopropanol (IPA) | 1.29 | 23.56 | 21.78 |
| Isopropyl Ether (IPE) | 82.42 | 44.51 | 49.76 |

TABLE 8-continued

Decomposition of IPE over Ce(IV) nitrate co-precipitated with zirconyl nitrate in presence of $H_2SO_4$

| Composition (wt. %) | Feed | Product Time on Stream (hrs) | |
|---|---|---|---|
| | | 50 | 65 |
| IPE Conversion (%) | | 49.1 | 43.1 |
| IPA Selectivity (%) | | 93.5 | 98.5 |
| IPA Yield (Per Pass) (%) | | 45.9 | 42.4 |

Example 21

IPE Decomposition Over Ce(III) Nitrate Co-Precipitated with Zirconyl Nitrate in Presence of Sulfuric Acid The decomposition of IPE was investigated in a fixed-bed microreactor. 0.5 grams of the catalyst of Example 10 were loaded into a ⅜" O.D. stainless steel reactor and dried with $N_2$ at 210° C. A sample of isopropyl ether (IPE) from the Baton Rouge Chemical Plant (same grade as in Example 12) was fed to the reactor at a WHSV of 5 $h^{-1}$. In addition, HPLC grade water was co-fed to the reactor at an IPE:$H_2O$ molar ratio of 1:0.8. Reactor temperature was 210° C. and pressure was 90 psig. The data for IPE conversion and IPA yields are shown in Table 9, demonstrating again that the catalyst prepared using separate sources of cerium(III), zirconium and sulfate has significant activity for IPE conversion to IPA.

TABLE 9

Decomposition of IPE over Ce(III) nitrate co-precipitated with zirconyl nitrate in presence of $H_2SO_4$

| Composition (wt. %) | Feed | Product Time on Stream (hrs) 20 |
|---|---|---|
| Propylene | 1.13 | 16.88 |
| Isopropanol (IPA) | 1.29 | 25.53 |
| Isopropyl Ether (IPE) | 82.42 | 43.25 |
| IPE Conversion (%) | | 47.6 |
| IPA Selectivity (%) | | 105.1 |
| IPA Yield (Per Pass) (%) | | 50.0 |

Example 22

IPE Decomposition Over Ce(IV) Nitrate Co-Precipitated with Zirconyl Nitrate in Presence of Sulfuric Acid Using High Solids Preparation The decomposition of IPE was investigated in a fixed-bed microreactor. 0.5 grams of the catalyst of Example 11 were loaded into a ⅜" O.D. stainless steel reactor and dried with $N_2$ at 210° C. A sample of isopropyl ether (IPE) from the Baton Rouge Chemical Plant (same grade as in Example 12) was fed to the reactor at a WHSV of 5 $h^{-1}$. In addition, HPLC grade water was co-fed to the reactor at an IPE:$H_2O$ molar ratio of 1:0.8. Reactor temperature was 210° C. and pressure was 90 psig. The data for IPE conversion and IPA yields are shown in Table 10, demonstrating again that the catalyst prepared from separate sources of cerium, zirconium, and sulfate has significant activity for IPE conversion to IPA.

TABLE 10

Decomposition of IPE over Ce(IV) nitrate co-precipitated with zirconyl nitrate in presence of $H_2SO_4$ using a high solids preparation

| Composition (wt. %) | Feed | Product Time on Stream (hrs) | |
|---|---|---|---|
| | | 20 | 50 |
| Propylene | 1.13 | 13.28 | 11.44 |
| Isopropanol (IPA) | 1.29 | 21.66 | 19.07 |
| Isopropyl Ether (IPE) | 82.42 | 51.10 | 55.59 |
| IPE Conversion (%) | | 38.3 | 32.9 |
| IPA Selectivity (%) | | 109.30 | 111.2 |
| IPA Yield (Per Pass) (%) | | 41.8 | 36.5 |

An important feature illustrated by the above examples is that using a recipe with cerium sulfate, the solids content is limited by the solubility of cerium sulfate salt to about 7 wt % or less. Adding sulfuric acid to cerium sulfate either neat or complexed doesn't significantly improve solubility or allow higher solids and produces an inferior catalyst. Thus, the preferred method of making the catalyst of the present invention is adding sulfuric acid to a cerium nitrate solution which provides improved solubility and allows higher solids content preparations and independent control of the cerium and sulfate content. The improved solubility allows solids content of the slurry recovered from the coprecipitation to be increased well above 7 wt %. In preferred embodiments the solids content of said slurry is at least about 10 wt %, more preferably at least about 14 wt %, still more preferably at least about 18 wt %, still more preferably at least about 20 wt %.

The following examples are directed to commercially available ceria-zirconia catalysts.

Comparative Example 23

A sample of a ceria-zirconia having a nominal 15% ceria content was obtained from Grace Davison. The decomposition of IPE over this catalyst was investigated in a fixed-bed microreactor. 0.5 grams of the Grace Davison catalyst were loaded into a ⅜" O.D. stainless steel reactor and dried with $N_2$ at 210° C. A sample of isopropyl ether (IPE) from the Baton Rouge Chemical Plant (same grade as in Example 12) was fed to the reactor at a WHSV of 5 $h^{-1}$. In addition, HPLC grade water was co-fed to the reactor at an IPE:$H_2O$ molar ratio of 1:1. Reactor temperature was 210° C. and pressure was 90 psig.

The reactor was run for 24 hours. IPE conversion was <1% throughout, and IPA yields were approximately zero. The data show that despite being similar in ceria content to the catalysts according to the present invention, the commercially available catalyst was inactive for IPE decomposition.

Comparative Example 24

A sample of a ceria-zirconia having a nominal 17.5% ceria content was obtained from Magnesium Electron Inc. The decomposition of IPE over this catalyst was investigated in a fixed-bed microreactor. 0.5 grams of the MEI catalyst were loaded into a ⅜" O.D. stainless steel reactor and dried with $N_2$ at 210° C. A sample of isopropyl ether (IPE) from the Baton Rouge Chemical Plant (same grade as in Example 12) was fed to the reactor at a WHSV of 5 $h^{-1}$. In addition, HPLC grade water was co-fed to the reactor at an IPE:$H_2O$ molar ratio of 1:1. Reactor temperature was 210° C. and pressure was 90 psig.

The reactor was run for 24 hours. IPE conversion was <1% throughout, and IPA yields were approximately zero. The data show that despite being similar in ceria content to the catalysts according to the present invention, the commercial catalyst was inactive for IPE decomposition.

Trade names used herein are indicated by a ™ symbol or ® symbol, indicating that the names may be protected by certain trademark rights, e.g., they may be registered trademarks in various jurisdictions.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention has been described above with reference to numerous embodiments and specific examples. Many variations will suggest themselves to those skilled in this art in light of the above detailed description. All such obvious variations are within the full intended scope of the appended claims. That being said, it will be understood that preferred embodiments of the present invention include Particularly preferred are: a method of making an acidic mixed metal oxide having the composition described by formula (1):

$$X_m Y_n Z_p O_q$$

wherein X is at least one metal selected from Group 4 of the Periodic Table of Elements, Y is at least one metal selected from Group 3 (including the Lanthanides and Actinides) of the Periodic Table of Elements, S is sulfur, and O is oxygen; m, n, p and q are the atomic ratios of their respective components and, when m is 1, n is from about 0.01 to about 0.75, p is 0.01 to about 0.50, and q is the number of oxygen atoms necessary to satisfy the valence of the other components made by coprecipitating X and Y from separate salts in the presence of a sulfur-containing species (also contemplating preferred ranges of these atomic ratios as set forth hereinabove); a process for selectively converting a dialkyl ether to the corresponding alkene and alkanol, the process comprising contacting a feed containing at least one dialkyl ether with a catalyst comprising an acidic mixed metal oxide having the compositioin of formula (1):

$$X_m Y_n Z_p O_q$$

wherein X is at least one metal selected from Group 4 of the Periodic Table of Elements, Y is at least one metal selected from Group 3 (including the Lanthanides and Actinides) of the Periodic Table of Elements, S is sulfur, and O is oxygen; m, n, p and q are the atomic ratios of their respective components and, when m is 1, n is from about 0.01 to about 0.75, p is 0.01 to about 0.50, and q is the number of oxygen atoms necessary to satisfy the valence of the other components made by coprecipitating X and Y from separate salts in the presence of a sulfur-containing species (again, contemplating also the preferred atomic ratios set forth hereinabove); a process for selectively converting a dialkyl ether to the corresponding alkene and alkanol, the process comprising contacting a feed containing at least one dialkyl ether with a catalyst comprising a cerium-zirconium catalyst in the presence of water, wherein said cerium-zirconium catalyst is made by a process comprising coprecipitating cerium and zirconium from separate salts in the presence of sulfate ions; a method of making a cerium-zirconium mixed oxide comprising coprecipitating cerium and zirconium from separate salts in the presence of sulfate ions; a method of making IPA comprising contacting IPE with a catalyst comprising a mixed cerium-zirconium oxide catalyst in the presence of water, wherein said cerium-zirconium catalyst is made by the process of coprecipitating cerium and zirconium from separate salts in the presence of sulfate ions; any of the aforementioned embodiments of which may be further characterized by one or more of the following, which may be applied as would be readily apparent to one of ordinary skill in the art in possession of the present disclosure: said cerium-zirconium catalyst is made by a process further comprising: (a) contacting a solution containing X, Y, and S ions (particularly cerium, zirconium, and sulfate ions, respectively) with a basic solution to form a slurry; (b) recovering said slurry; (c) filtering said slurry to recover a filtercake; (d) drying and calcining said filtercake to obtain said cerium-zirconium mixed oxide (which may be further characterized, in a still more preferred embodiment, by: wherein after step (b) and before step (c) said slurry is aged at a predetermined temperature for a predetermined period of time, such as for a period of about 5 hours to about 200 hours at a temperature of from about 50 to about 250° C., for a period of about 20 hours to about 100 hours at a temperature of from about 50 to about 200° C., for a period of about 20 hours to about 72 hours at a temperature of from about 75 to about 150° C.); and also wherein said basic solution is an aqueous amonium hydroxide solution; wherein X is zirconyl nitrate; wherein Y is cerium sulfate, wherein Y is provided by is provided in the form of a sulfuric acid complex, especially preferred being a sulfuric acid complex of a cerium salt; wherein at least one source of S is the sulfate ion $SO_4^{-2}$, and more particularly wherein the sulfate ion is sulfuric acid, ammonium sulfate, sodium sulfate, or a mixture thereof, and even more particularly wherein the source of sulfate ion consists essentially of sulfuric acid, ammonium sulfate, sodium sulfate, or a combination thereof; and also wherein Y is cerium and is provided by is a cerium(III) salt and/or a cerium (IV) salt; and where Y is cerium and is provided by cerium nitrate. Another preferred embodiment includes use of the catalyst comprising the material described by formula (1) in other reactions wherein certain feeds, which may include exhaust gases (especially exhaust gases from an internal combustion engine) contact said catalyst.

We claim:

1. A method of making isopropyl alcohol comprising contacting isopropyl ether with a catalyst comprising a mixed cerium-zirconium oxide catalyst in the presence of water, wherein said cerium-zirconium oxide catalyst is made by the process of coprecipitating cerium and zirconium form separate salts in the presence of sulfate ions wherein said catalyst has the following composition:

$$X_m Y_n S_p O_q$$

wherein X is at least one metal selected from Group 4 of the Periodic Table of Elements, Y is at least one metal selected from Group 3 (including the Lanthanides and Actinides) of the Periodic Table of Elements, S is sulfur, and O is oxygen; m, n, p and q are the atomic ratios of their respective components and, wherein the ratio of elements in said composition is such that when m is 1, n is from about 0.10 to about 0.35, p is 0.01 to about 0.50, and q is the number of oxygen atoms necessary to satisfy the valence of the other components made by coprecipitating X and Y from separated salts in the presence of a sulfur-containing species.

2. A method of making an acidic mixed metal oxide having the following composition:

$$X_m Y_n S_p O_q$$

wherein X is at least one metal selected from Group 4 of the Periodic Table of Elements, Y is at least one metal selected from Group 3 (including the Lanthanides and Actinides) of the Periodic Table of Elements, S is sulfur, and O is oxygen; m, n, p and q are the atomic ratios of their respective components and, wherein the ratio of elements in said composition is such that when m is 1, n is from about 0.10 to about 0.35, p is 0.01 to about 0.50, and q is the number of oxygen atoms necessary to satisfy the valence of the other components made by the method comprising the steps of
 (a) coprecipitating X and Y from separate salts in the presence of a sulfur-containing species;
 (b) contacting a solution containing X, Y, and sulphur-containing species with a basic solution to form a slurry;
 (c) recovering said slurry;
 (d) aging said slurry at 50 to about 250° C. for a predetermined period of time;
 (e) filtering said slurry to recover a filtercake; and
 (f) drying and calcining said filtercake to obtain said acidic mixed metal oxide wherein said acidic mixed metal oxide is used as a catalyst in a process for selectively converting a dialkyl ether to the corresponding alkene and alkanol.

3. The method of claim 2, wherein X is zirconium and Y is cerium.

4. The method of claim 2, wherein p is from about 0.10 to about 0.35.

5. The method of claim 2, wherein X is provided by zirconyl nitrate.

6. The method of claim 2, wherein Y is provided by cerium sulfate.

7. The method of claim 2, wherein Y is cerium and said cerium is provided in the form of a sulfuric acid complex of a cerium salt.

8. The method of claim 7, wherein said cerium salt is cerium sulfate.

9. The method of claim 2, wherein at least one source of S is sulfate, which is provided by at least one species selected form the group consisting of sulfuric acid, ammonium sulfate, and sodium sulfate, and wherein the source of sulfate ion consists essentially of sulfuric acid, ammonium sulfate, sodium sulfate, or a combination thereof.

10. The method of claim 2, wherein Y is provided by a cerium(III) salt.

11. The method of claim 2, wherein Y is provided by a cerium(IV) salt.

12. The method of claim 2, wherein Y is provided by cerium nitrate.

* * * * *